US007365060B2

(12) United States Patent
Rokita et al.

(10) Patent No.: US 7,365,060 B2
(45) Date of Patent: Apr. 29, 2008

(54) DINUCLEAR COPPER-BASED COMPOUND AND LIGAND FOR NUCLEIC ACID SCISSION AND ANTICANCER TREATMENT

(75) Inventors: Steven E. Rokita, Silver Spring, MD (US); Kenneth D. Karlin, Owings Mills, MD (US); Kristi J. Humphreys, Oakland, CA (US); Lei Li, Baltimore, MD (US); Narasimha N. Murthy, Madras (IN)

(73) Assignee: University of Maryland, College Park, MD (US)

( * ) Notice: Subject to any disclaimer, the term of this patent is extended or adjusted under 35 U.S.C. 154(b) by 62 days.

(21) Appl. No.: 10/492,196

(22) PCT Filed: Nov. 12, 2002

(86) PCT No.: PCT/US02/36083

§ 371 (c)(1),
(2), (4) Date: Nov. 16, 2004

(87) PCT Pub. No.: WO03/054145

PCT Pub. Date: Jul. 3, 2003

(65) Prior Publication Data
US 2005/0090479 A1    Apr. 28, 2005

Related U.S. Application Data

(60) Provisional application No. 60/331,197, filed on Nov. 9, 2001.

(51) Int. Cl.
*A61K 31/655* (2006.01)
(52) U.S. Cl. .................................... 514/151
(58) Field of Classification Search ............... 556/110; 514/449, 151
See application file for complete search history.

(56) References Cited

U.S. PATENT DOCUMENTS 6,765,104 B1 *  7/2004  Brechbiel et al. ........... 556/110

OTHER PUBLICATIONS

Cecil (Textbook of Medicine, 21st Edition (2000), Goldman & Bennett (Editors), W.B. Saunders Company (Publisher), Chapter 198, pp. 1060-1074).*

(Continued)

*Primary Examiner*—Ardin H. Marschel
*Assistant Examiner*—James D. Anderson
(74) *Attorney, Agent, or Firm*—Arent Fox LLP

(57) ABSTRACT

The present invention is related to a novel method for splitting nucleic acids at specific points on a complementary nucleic acid segment using a dinuclear copper-based compound of Formula I. Additionally, the present invention is related to a novel treatment of cancer, tumors, and cancer cells using a dinuclear copper-based compound of Formula I or a naked ligand of formula II: (Formula I and II).

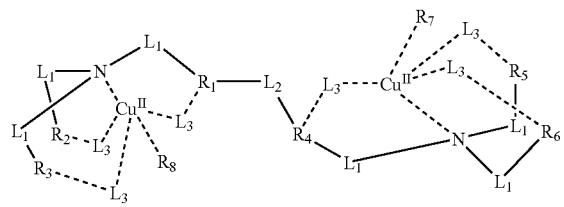

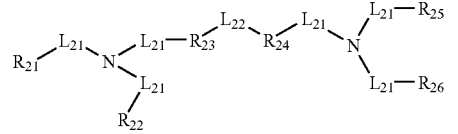

7 Claims, 1 Drawing Sheet

OTHER PUBLICATIONS

Lucchese B, et al. "Mono-, Bi-, and Trinclear CuII-CI containing products based on . . . ," 2004 Inorganic Chem 43(19): 5987-5998.*

Lee, Dong-Heon, et al. ("Binuclear Copper Complexes based on the 6,6'-Bis[[bis(2-pyridylmethyl)amino]methyl]-2,2'-bipyridine Ligand," 1997 Inorganic Chem 36: 5785-5792).*

Lee, Dong-Heon, et al. ("Reversible O2 binging to a dinuclear copper(I) complex with linked tris(2-pyridylmethyl)amine units," 1995 JACS 117: 12498-12513).*

Humphreys KJ, et al., "Targeted strand scission of DNA substrates by a Tricopper(II) coordination complex," 2002 JACS 124: 8055-8066 (provided on PTO From 1449).*

Humphreys KJ, et al., "Recognition and strand scission at junctions between single- and double-stranded DNA by a trinuclear copper complex," 2001 JACS 123: 5588-5589 (provided on PTO From 1449).*

"The CDER Handbook" Produced by the Dept. of Health and Human Services, Food and Drug Administration, Center for Drug Evaluation and Research <http://www.fda.gov/cder/handbook>, pp. 1-9, printed from the internet on Sep. 14, 2005."The CDER Handbook".*

Gura et al. Systems for Identifying New Drugs are Often Faulty. Science, 1997, 278:1041-1042.*

Johnson et al. Relationships between drug activity in NCI preclinical in vitro and in vivo models and early clinical trials. British J. of Cancer, 2001, 84(10):1424-1431.*

Kristi J. Humphreys et al; Recognition and Strand Scission at Junctions between Single-and Double-Stranded DNA by a Trinuclear Copper Complex; J. Am. Chem. Soc.; vol. 123; No. 23; 2001; pp. 5588-5589.

Kristi J. Humphreys et al; Targeted Strand Scission of DNA Substrates by a Tricopper (II) Coordination Complex; J. Am. Chem. Soc.; vol. 124; No. 27; 2001; pp. 8055-8066.

Kristi J. Humphreys et al; Efficient and Specific Strand Scission of DNA by a Dinuclear Copper Complex: Comparative Reactivity of Complexes with Linked Tris(2-pyridylmethyl)amine Moieties; J. Am. Chem. Soc. 2002; vol. 124; pp. 6009-6019.

* cited by examiner

Figure 1. Humphreys, *et al.*
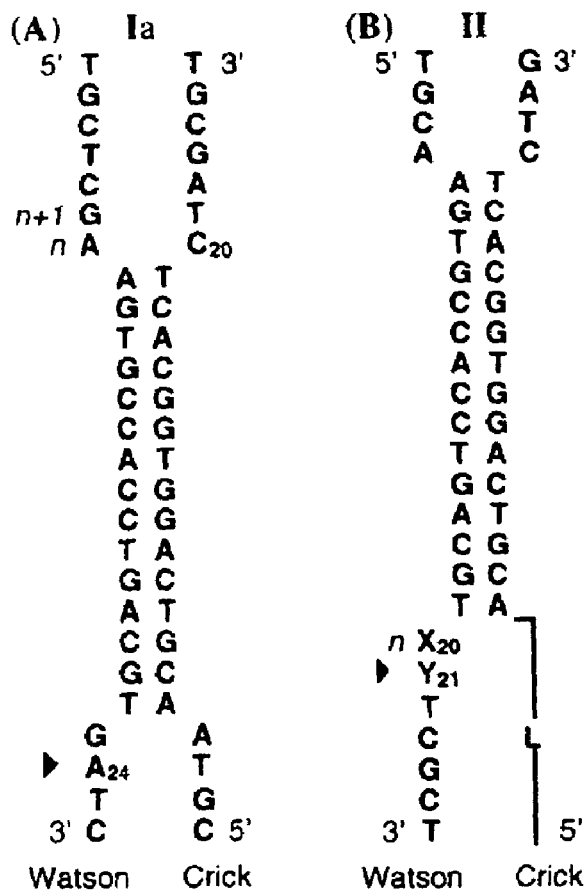

DINUCLEAR COPPER-BASED COMPOUND AND LIGAND FOR NUCLEIC ACID SCISSION AND ANTICANCER TREATMENT

This is a 371 of International Patent Application No. PCT/US02/36083 filed on Nov. 12, 2002, which is based on U.S. Provisional Application Ser. No. 60/331,197, filed on Nov. 9, 2001. The disclosure of the prior applications are hereby incorporated by reference herein in its entirety.

The United States Government has rights in this invention pursuant to Grants No. GM28962 and GM47351 awarded by the National Institutes of Health (NIH).

FIELD OF INVENTION

The present invention is related to a novel method for splitting nucleic acids at specific points on a nucleic acid segment using a dinuclear copper-based compound. Additionally, the present invention is related to a novel treatment of cancer, tumors, and cancer cells using a dinuclear copper-based compound or its naked ligand.

BACKGROUND OF INVENTION

A number of transition metal complexes have been found to be able to differentiate between double- vs. single-stranded DNA or B vs. Z helical forms of DNA through noncovalent recognition. This selectivity is primarily due to the binding of the transition metal complex in either the major or minor groove of duplex structures or in association with the nucleobases in unpaired strands. The electron-rich character of the nucleobases often makes them strong ligands for metals and efficient targets of oxidation. Guanine has been shown to have the highest affinity for coordination to transition metal ions and it is also the most easily oxidized, followed by adenine, cytosine and thymine (in order of ease of oxidation). Although base oxidation can be highly specific and directed to one site, strand scission has been shown to result from base oxidation only after treatment with subsequent heat and alkaline conditions.

However, direct strand scission does not necessarily require any special treatment to detect the sites of reaction. Some complexes that exhibit direct strand cleavage in conjunction with sequence specificity are bleomycin.Fe(II) and the metallointercalator, $[Rh(phen)_2phi]^{3+}$. Although there is both a structural and a sequence requirement in each of these cases, the recognition criteria are not sufficiently unique to limit the number of target sites in DNA. Scission may be targeted specifically to one site by incorporating known DNA recognition elements into the ligand suprastructure of a well-characterized nucleolytic agent such as EDTA.Fe(II), which, when underivatized, promotes oxidative cleavage of DNA in a random fashion without nucleotide sequence selectivity. While this approach localizes cleavage to a site where the recognition element binds to DNA, the reaction is rarely constrained to a single nucleotide. Strand cleavage frequently extends over more than 5 bases. A longstanding goal of considerable interest has been to construct transition metal complexes that can mediate direct and specific strand scission targeted to a single base with a significantly high level of recognition such that cleavage occurs at a limited number of sites along a target polynucleotide.

Most investigations focusing on oxidative strand scission of DNA by transition metals have typically relied on mononuclear complexes. Among these complexes, bis(1,10-phenanthroline)copper, $[Cu(OP)_2]^{2+}$, has been studied extensively due to its high nucleolytic efficiency. The cleavage pattern induced by $[Cu(OP)_2]^{2+}$ is predominantly sequence-neutral, although some variability in intensity due to local perturbations of DNA structure affects its efficiency. Also a slight, but distinct, preference for cleavage at 5'-AT-3' and 5'-GT-3' sites has been observed. Otherwise, $[Cu(OP)_2]^{2+}$ like EDTA.Fe(II) may be conjugated to binding elements such as proteins and complementary sequences of RNA or DNA that possess affinity for specific sites on DNA. Still, multiple sites adjacent to the locus of recognition are typically oxidized by these complexes even when tethered to a DNA recognition element.

SUMMARY OF INVENTION

The present invention is based on the discovery that certain dinuclear copper-based compounds possess the ability to recognize and promote scission of a nucleic acid at specific positions. Additionally, it has been discovered that the dinuclear copper-based compounds and the naked ligand possess the ability to treat cancer.

Thus, the invention is directed towards a method of treating cancer in a patient in need thereof, comprising administering to a patient a cancer-treating effective amount of a compound of formula I,

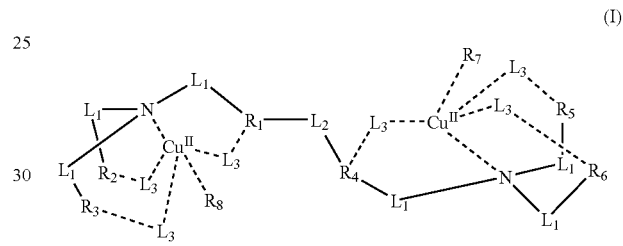

(I)

wherein:

$R_1$-$R_6$ are each independently (a) a 5 to 6 membered heterocycle containing 1-3 nitrogen atoms and optionally one oxygen atom, with the remainder of the atoms being carbon atoms, wherein the heterocycle is linked to a respective linkage $L_3$ through a nitrogen atom of the heterocycle, and wherein the heterocycle is linked to a respective linkage $L_1$ through any of the nitrogen or carbon atoms of the heterocycle other than the nitrogen atom that links to linkage $L_3$; and wherein the 5 to 6 membered heterocycle is unsubstituted or substituted with 1-3 substituents selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide or (b) an aromatic or cycloalkyl $C_9$-$C_{13}$ bicycle containing 1-3 nitrogen atoms and optionally one oxygen atom, with the remainder of the atoms being carbon atoms, wherein the bicycle is linked to a respective linkage $L_3$ through a nitrogen atom of the bicycle, and wherein the bicycle is linked to a respective linkage $L_1$ through any of the nitrogen or carbon atoms of the bicycle other than the nitrogen atom that links to linkage $L_3$, and wherein said aromatic or cycloalkyl $C_9$-$C_{13}$ bicycle is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide;

$R_7$-$R_8$ are each independently an anion or uncharged species;

each $L_1$ is independently a $C_1$-$C_6$ alkyl or ether linkage;

each $L_3$ is a direct bond; and $L_2$ is independently selected from the group consisting of (a) a $C_1$-$C_6$ alkyl which may optionally be interrupted with one or more ether linkages, wherein the $C_1$-$C_6$ alkyl is unsubstituted or substituted with 1 to 3 substituents each independently selected from the group consisting of halogen, hydroxy, formyloxy, azido, carboxyl, cyano, amino, $C_1$-$C_4$ alkoxy, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; (b) an ether linkage; (c) an aromatic or cycloalkyl $C_5$-$C_8$ monocycle which is unsubstituted or substituted with 1 to 3 substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; and (d) an aromatic or cycloalkyl $C_9$-$C_{13}$ bicycle which is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide.

The invention is further directed towards a method of treating a cancer tumor, said method comprising administering to the cancer tumor a cancer tumor-treating effective amount of a compound of formula I.

The invention is additionally directed towards a method of treating cancer cells, said method comprising administering to the cancer cells a cancer cell-treating effective amount of a compound of formula I.

The invention is further directed towards a use of a compound of formula I to treat cancer.

The invention is further directed towards a compound of formula I.

The invention is further directed towards the use of a compound of formula I to prepare a medicament suitable for treating cancer.

The invention is further directed towards a method of splitting a nucleic acid segment at a specific position thereon, wherein said method comprises (A) providing a nucleic acid segment having (i) an n position, wherein said n position is (a) the first unpaired position on the 3' overhang of the nucleic acid segment, (b) adjacent to the point of scission, and (c) occupied by a guanine residue, (ii) an x position, wherein said x position is (a) the first unpaired position on the 5' overhang of the nucleic acid segment, and (b) occupied by an adenine residue, and (iii) an n+1 position wherein said n+1 position is the point of scission and is the first unpaired residue that is adjacent to the n position and (B) contacting the nucleic acid segment with a compound of formula I for a time sufficient to split the nucleic acid at the n+1 position of the nucleic acid segment.

The invention is further directed towards a method of treating cancer in a patient in need thereof, said method comprising administering to a patient a cancer-treating effective amount of a compound of formula II,

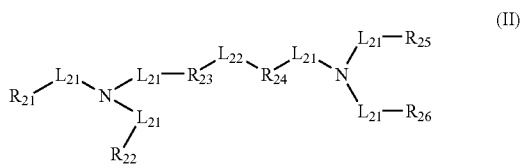

wherein:

$R_{21}$-$R_{26}$ are each independently (a) a 5 to 6 membered heterocycle containing 1-3 nitrogen atoms and optionally one oxygen atom, with the remainder of the atoms being carbon atoms, wherein the heterocycle is linked to a respective linker $L_{21}$ through a carbon or nitrogen atom of the heterocycle; and wherein the 5 to 6 membered heterocycle is unsubstituted or substituted with halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, phenyloxycarbonylamino, naphthyloxycarbonylamino, semicarbazido, heteroaryl, 4-acetoxyphenyloxy, phenyl or acetamide or (b) an aromatic or cycloalkyl $C_9$-$C_{13}$ bicycle containing 1-3 nitrogen atoms and optionally one oxygen atom, with the remainder of the atoms being carbon atoms, wherein the bicycle is linked to a respective linkage $L_{21}$ through a nitrogen atom of the bicycle, and wherein said aromatic or cycloalkyl $C_9$-$C_{13}$ bicycle is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide;

each $L_{21}$ is independently $C_1$-$C_6$ alkyl or ether linkage; and $L_{22}$ is independently selected from the group consisting of (a) a $C_1$-$C_6$ alkyl which may optionally be interrupted with one or more ether linkages, wherein the $C_1$-$C_6$ alkyl is unsubstituted or substituted with 1 to 3 substituents each independently selected from the group consisting of halogen, hydroxy, formyloxy, azido, carboxyl, cyano, amino, $C_1$-$C_4$ alkoxy, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; (b) an ether linkage; (c) an aromatic or cycloalkyl $C_5$-$C_8$ monocycle which is unsubstituted or substituted with 1 to 3 substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; and (d) an aromatic or cycloalkyl $C_9$-$C_{13}$ bicycle which is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide.

The invention is further directed towards a method of treating a cancer tumor, said method comprising administering to the cancer tumor a cancer tumor-treating effective amount of a compound of formula II.

The invention is further directed towards a method of treating cancer cells, said method comprising administering to the cancer cells a cancer cell-treating effective amount of a compound of formula II.

The invention is further directed towards a use of a compound of formula II to treat cancer.

The invention is further directed towards a compound of formula II.

The invention is further directed towards the use of a compound of formula II to prepare a medicament suitable for treating cancer.

The invention is also directed towards a pharmaceutical composition containing a pharmaceutically effective amount of at least one compound of formula I.

The invention is also directed towards a pharmaceutical composition containing a pharmaceutically effective amount of at least one compound of formula II.

BRIEF DESCRIPTION OF THE DRAWINGS

FIG. 1 illustrates two DNA strands and the points of scission on each with the claimed complexes.

DETAILED DESCRIPTION OF THE PREFERRED EMBODIMENTS

The present invention is directed to novel uses of dinuclear copper-based compounds and the naked ligand thereof.

The term "nucleic acid" includes double-stranded or single-stranded DNA and RNA.

The term "segment" is intended to define either (1) a region of a nucleic acid sequence on a nucleic acid strand or (2) an entire nucleic acid strand, whether (1) or (2) be double-stranded or single-stranded.

The term "n position" is intended to define a position on a nucleic acid segment that possesses the following properties: (a) said position is the first unpaired position on the 3' overhang of the nucleic acid segment, and (b) said position is occupied by a guanine residue.

The term "x position" is intended to define a position on a nucleic acid segment that possesses the following properties: (a) said position is the first unpaired position on the 5' overhang of the nucleic acid segment, (b) said position is adjacent to the point of scission, and (c) said position is occupied by an adenine residue.

The term "n+1 position" is intended to define a position on a nucleic acid segment that is the first unpaired residue on the 3' overhang that is adjacent to the n position and which is the point of scission.

In the compound of formula I, the groups labeled $R_1$-$R_6$ can each be independently a 5 to 6 membered heterocycle containing 1-3 nitrogen atoms and optionally one oxygen atom, with the remainder of the atoms being carbon atoms. These heterocycles include, but are not limited to, pyrrolyl, 2-H pyrrolyl, 3H-pyrrolyl, pyrazolyl, 2H-imidazolyl, 1,2,3-triazolyl, 1,2,4-triazolyl, isoxozolyl, oxazolyl, 1,2,3-oxadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, pyridyl, pyridazyl, pyrimidinyl, pyrazyl, piperazyl, 1,3,5-trazyl, 1,2,4-triazyl, 1,2,3-triazyl, 4H-1,2-oxazyl, 2H-1,3-oxazyl, 6H-1,3-oxazyl, 6H-1,2-oxazyl, 1,4-oxazyl, 2H-1,2-oxazyl, 4H-1,4-oxazyl, 1,2,4-oxadiazyl, 1,3,5-oxadiazyl, pyrrolidinyl, piperidinyl, piperazinyl, pyrazinyl, 1,2,3,6-tetrahydropyridinyl, pyrazolinyl, pyrazolidinyl, pyridinyl, pyrazolyl, triazolyl, pyrazinyl, oxazolyl, pyridazinal, triazinyl, and morpholyl.

The 5 to 6 membered heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

Additionally, in the compound of formula I, the groups labeled $R_1$-$R_6$ can each be independently a 9-13 membered bicyclic heterocycle containing 1-3 nitrogen atoms and optionally one oxygen atom, with the remainder of the atoms being carbon atoms. These bicyclic heterocycles include, but are not limited to, indolyl, 3H-indolyl, cyclopenta[b]pyridinyl, pyrano[3,4-b]-pyrrolyl, indazolyl, benzisoxazolyl, benzoxazolyl, quinolinyl, isoquinolinyl, cinnolinyl, quinazolinyl, 1,8-naphthyridinyl, 1,7-naphthyridinyl, 1,6-naphthyridinyl, 2H-1,3-benzoxazine, 2H-1,4-benzoxazine, 1H-2,3-benzoxazine, 4H-3,1-benzoxazine, 2H-1,2-benzoxazine, and 4H-1,4-benzoxazine.

The 9-13 membered bicyclic heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

In formula I, groups $R_7$-$R_8$ are each independently an anion or uncharged species. Any physiologically acceptable or pharmaceutically acceptable anion can be used as a substituent for $R_7$-$R_8$. Said acceptable anions include, but are not limited to, any thiolate, nitrate, chloride, acetate, perchlorate, phosphate, bromide, fluoride, iodide, sulfate, trifluoromethanesulfonate, hexafluorophosphate, hexafluoroantimonate or any halide anion.

Additionally, in formula I, each $L_1$ is independently $C_1$-$C_6$ alkyl or ether linkage, and $L_3$ is a direct bond. It is preferred that the $C_1$-$C_6$ alkyl linkage be a methyl or ethyl linkage. It is also preferred that the $L_1$ linkage is linked to a carbon atom of the heterocycle. $L_2$ is independently selected from the group consisting of (a) a $C_1$-$C_6$ alkyl which may optionally be interrupted with one or more ether linkages, wherein the $C_1$-$C_6$ alkyl is unsubstituted or substituted with 1 to 3 substituents each of which is independently selected from the group consisting of halogen, hydroxy, formyloxy, azido, carboxyl, cyano, amino, $C_1$-$C_4$ alkoxy, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; (b) an ether linkage; (c) an aromatic or cycloalkyl $C_5$-$C_8$ monocycle which is unsubstituted or substituted with 1 to 3 substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; and (d) an aromatic or cycloalkyl $C_9$-$C_{13}$ bicycle which is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide.

All references to "halogen" include fluorine, chlorine, bromine, and iodine. All references to the alkyl groups include branched or unbranched alkyl groups. All references to "heteroaryl" are intended to include a monocyclic aromatic hydrocarbon group having 5 or 6 ring atoms, or a bicyclic aromatic group having 8 to 10 atoms, each containing 1-3 heteroatoms selected from O, S or N, with the remainder of the atoms being carbon. Examples of suitable heteroaryls include pyridinyl, pyrimidinyl, and pyrazinyl, pyridazinyl, pyrrolyl, furanyl, oxazolyl, isoxazolyl, thiazolyl, isobenzofuryl, benzofuryl, benzo[b]thiophenyl, benzo[c]thiophenyl, indolyl, 3H-indolyl, 1H-indolyl, cyclopenta[b]pyridinyl, pyrano[3,4-b]pyrrolyl, indazolyl, benzisoxazolyl, benzoxazolyl, 2,1-benzisoxazolyl, 2H-1-benzopyranyl, 2H-1-benzoyran-2-yl, 4H-1-benzopyran-4-yl, 1H-2-benzopyran-1-yl, 3H-2-benzopyran-1-yl, quinolinyl, isoquinolinyl, cinnolinyl, quinazolinyl, 1,8-napthtyridinyl, 1,7-napthtyridinyl, 1,5-napthtyridinyl, 1,6-napthtyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, and the like.

In the compound of formula II, groups $R_{21}$-$R_{26}$ can each be independently a 5 to 6 membered heterocycle containing 1-3 nitrogen atoms and optionally one oxygen atom, with the remainder of the atoms being carbon atoms. These heterocycles include, but are not limited to, pyrrolyl, 2-H pyrrolyl, 3H-pyrrolyl, pyrazolyl, 2H-imidazolyl, 1,2,3-triazolyl, 1,2,4-triazolyl, isoxozolyl, oxazolyl, 1,2,3-oxadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, pyridyl, pyridazyl, pyrimidinyl, pyrazyl, piperazyl, 1,3,5-triazyl, 1,2,4-triazyl, 1,2,3-triazyl, 4H-1,2-oxazyl, 2H-1,3-oxazyl, 6H-1,3-oxazyl, 6H-1,2-oxazyl, 1,4-oxazyl, 2H-1,2-oxazyl, 4H-1,4-oxazyl, 1,2,4-oxadiazyl, 1,3,5-oxadiazyl, pyrrolidinyl, piperidinyl, piperazinyl, pyrazinyl, 1,2,3,6-tetrahydropyridinyl, pyrazolinyl, pyrazolidinyl, pyridinyl, pyrazolyl, triazolyl, pyrazinyl, oxazolyl, pyridazinal, triazinyl, and morpholyl.

The 5 to 6 membered heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ allyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

Additionally, in the compound of formula II, the groups labeled $R_{21}$-$R_{26}$ can each be independently a 9-13 membered bicyclic heterocycle containing 1-3 nitrogen atoms and optionally one oxygen atom, with the remainder of the atoms being carbon atoms. These bicyclic heterocycles include, but are not limited to, indolyl, 3H-indolyl, cyclopenta[b]pyridinyl, pyrano[3,4-b]-pyrrolyl, indazolyl, benzisoxazolyl, benzoxazolyl, quinolinyl, isoquinolinyl, cinnolinyl, quinazolinyl, 1,8-naphthyridinyl, 1,7-naphthyridinyl, 1,6-naphthyridinyl, 2H-1,3-benzoxazine, 2H-1,4-benzoxazine, 1H-2,3-benzoxazine, 4H-3,1-benzoxazine, 2H-1,2-benzoxazine, and 4H-1,4-benzoxazine.

The 9-13 membered bicyclic heterocycle is either unsubstituted or substituted with 1 to 3 substituents selected from halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide.

Additionally, in formula II, each $L_{21}$ linkage is independently a $C_1$-$C_6$ alkyl, or ether linkage. Preferably, the $L_{21}$ linkage is linked to a carbon atom of the heterocycle. It is also preferred that the $C_1$-$C_6$ alkyl linkage is a methyl or ethyl linkage. Each $L_{22}$ is independently (a) a $C_1$-$C_6$ alkyl which may optionally be interrupted with one or more ether linkages, wherein the $C_1$-$C_6$ alkyl is unsubstituted or substituted with 1 to 3 substituents each of which is independently selected from the group consisting of halogen, hydroxy, formyloxy, azido, carboxyl, cyano, amino, $C_1$-$C_4$ alkoxy, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; (b) an ether linkage; (c) an aromatic or cycloalkyl $C_5$-$C_8$ monocycle which is unsubstituted or substituted with 1 to 3 substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl and acetamide; and (d) an aromatic or cycloalkyl $C_9$-$C_{13}$ bicycle which is unsubstituted or substituted with 1 to 3 substituents, said substituents each independently selected from the group consisting of halogen, hydroxy, formyloxy, azido, carboxyl, cyano, amino, $C_1$-$C_4$ alkoxy, $C_1$-$C_4$ alkyl, benzyl, nitro, $C_1$-$C_4$ acylamino, formyl, formamido, thioformamido, $C_1$-$C_4$ alkoxycarbonylamino, $C_1$-$C_4$ alkoxycarbonyl, phenyloxycarbonylamino, naphthyloxycarbonylamino, semicarbazido, heteroaryl, 4-acetoxyphenyloxy, phenyl or acetamide.

All references to "halogen" include fluorine, chlorine, bromine, and iodine. All references to the alkyl groups include branched or unbranched alkyl groups. All references to "heteroaryl" are intended to include a monocyclic aromatic hydrocarbon group having 5 or 6 ring atoms, or a bicyclic aromatic group having 8 to 10 atoms, each containing 1-3 heteroatoms selected from O, S or N, with the remainder of the atoms being carbon. Examples of suitable heteroaryls include pyridinyl, pyrimidinyl, and pyrazinyl, pyridazinyl, pyrrolyl, furanyl, oxazolyl, isoxazolyl, thiazolyl, isobenzofuryl, benzofuryl, benzo[b]thiophenyl, benzo[c]thiophenyl, indolyl, 3H-indolyl, 1H-indolyl, cyclopenta[b]pyridinyl, pyrano[3,4-b]pyrrolyl, indazolyl, benzisoxazolyl, benzoxazolyl, 2,1-benzisoxazolyl, 2H-1-benzopyranyl, 2H-1-benzoyran-2-yl, 4H-1-benzopyran-4-yl, 1H-2-benzopyran-1-yl, 3H-2-benzopyran-1-yl, quinolinyl, isoquinolinyl, cinnolinyl, quinazolinyl, 1,8-napthtyridinyl, 1,7-napthtyridinyl, 1,5-napthtyridinyl, 1,6-napthtyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, and the like.

The compounds of formula I have been found to be effective in treating cancer. Some types of cancer that the compounds of formulas I and II have been found to be effective in treating are leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer. The compounds of formulas I and II are, therefore, suitable for use in methods for treating cancer, cancer cells, or tumors, whether the compound of formula I or II is used alone or in conjunction with another compound of formula I or formula II or another known anti-cancer agent.

Such methods comprise administering to a patient in need of such treatment an anti-cancer, anti-tumor, or anti-cancer cell effective amount (hereinafter "effective amount") of one or more compounds of formulas I and/or II. The effective amount of the compound(s) of formulas I and/or II are preferably administered in any conventional form suitable for oral administration, for example in the form of a tablet, caplet, capsule, beadlet or powder. Additionally, dosage forms include troches, dispersions, suspensions, solutions, injections, infusions, creams, ointments, aerosols, and the like. These administration forms may be presented in unit dosage form and may be prepared by any of the methods well-known in the art of pharmacy. The compound(s) of formula I and/or II is/are present in an amount of from 1 to 99% by weight, based upon the total weight of the dosage form, for example from 10 to 50% by weight.

Additionally, the compound(s) of formula I and/or II can be administered in any other form suitable for rectal, topical, parenteral, intraperitoneal, ocular, pulmonary, inhalation, intramuscular, intravenous, and vaginal administration. The compound(s) of formula I and/or formula II is/are present in the dosage form in an amount of from 1 to 99% by weight, based upon the total weight of the dosage form, for example from 10 to 50% by weight.

The magnitude of a dose administered, however, varies according to the age, weight, sex, and response of the individual patient. In general, the daily dose range of a compound of formula I or II (or of any mixture thereof) is within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases. These dosages may fall within the range of 0.00001 to 500 mg administered to the patient per day. When the composition is in the form of an oral composition, the weight of the compound(s) of formula I and/or formula II in the composition may be in the range of from 0.00001 to 500 mg, such as from 5 to 250 mg or from 10 to 200 mg. If the compound(s) of formula I and/or formula II is/are in the form of a tablet, the tablet may be uncoated or coated and the coating may be a conventional coating and the coating may be applied by a conventional method.

A pharmaceutical composition with a compound (or compounds) of formula I and/or formula II as an active ingredient (or a pharmaceutically acceptable salt thereof), may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. Said pharmaceutical composition contains a pharmaceutically effective amount of at least one compound of formula I and/or formula II. Further, the pharmaceutical composition is pharmaceutically effective against cancer, including leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer.

The dosage may be administered in either one single dosage, two dosages, or in more than two dosages per day.

The compounds of formula I and formula II have been found to exhibit a remarkable ability to promote specific strand scission at junctions between single- and double-stranded DNA. Strand scission occurs at the n+1 position and is not dependent on the identity of the base at which cleavage occurs.

Scission minimally requires a guanine in the n position and an adenine in the x position. Selective strand scission is preferably conducted in the presence of dioxygen.

The time required to split the nucleic acid is normally between 0 (instant) and 60 minutes. However, the time required to split the nucleic acid may be adjusted according to the composition of the nucleic acid segments and the presence and amount of dioxygen. The nucleic acid segment is preferably longer than 5 nucleotides in length, and the nucleic acid segment may comprise an entire chromosome. However, the nucleic acid segment is preferably between 5 and 100,000 nucleotides in length, even more preferably between 5 and 50,000 nucleotides in length, even further preferred is a segment that is between 5 and 10,000 nucleotides in length, and most preferred is a segment that is between 5 and 1,000 nucleotides in length. Also preferred are segments of between 10, 20, or 30 and 1,000 nucleotides in length.

The following are incorporated by reference in their entirety:
1) "Recognition and Strand Scission at Junctions between Single- and Double-stranded DNA by a Trinuclear Copper Complex" by Kristi J. Humphreys, Kenneth D. Karlin, and Steven E. Rokita, J. Am. Chem Soc. 2001, 123, 5588-5589.
2) The Handbook of Chemistry and Physics (82nd Edition) edited by David R. Lide.
3) "A new trinuclear complex and its reactions with plasmid DNA" by Steven T. Frey, Helen H. J. Sun, Narasimha N. Murthy, and Kenneth D. Karlin, Inorganica Chimica Acta 242 (1996) 329-338.
4) "Targeted Strand Scission of DNA Substrates by a Tricopper II Coordination Complex" by Kristi J. Humphreys, Kenneth D. Karlin, and Steven E. Rokita, J. Am. Chem Soc. 2002, 124, p. 8055-8066.
5) "Goodman and Gilman's The Pharmaceutical Basis of Therapeutics" edited by Alfred Goodman Gilman, Theodore W. Rall, Alan S. Nies, and Palmer Taylor (8th Edition).
6) "Goodman and Gilman's The Pharmaceutical Basis of Therapeutics" edited by Joel G. Hardman, Lee E. Limbard, Perry B. Molinoff, Raymond W. Ruddon (9th Edition).
7) "Goodman and Gilman's The Pharmaceutical Basis of Therapeutics" edited by Joel G. Hardman, Lee E. Limbard, and Alfred Goodman Gilman (10th Edition).
8) U.S. Provisional Application No. 60/331,197.
9) U.S. Provisional Application No. 60/331,198.
10) "Oxidative strand scission of nucleic acids by a multinuclear copper (II) complex" by Kristi J. Humphreys, Anne E. Johnson, Kenneth D. Karlin, and Steven E. Rokita, J. Biol. Inorg. Chem. (2002) 7: 835-842.
11) "Efficient and Specific Strand Scission of DNA by a Dinuclear Copper Complex: Comparative Reactivity of Complexes with Linked ris(2-pyridylmethyl)amine Moieties" by Kristi J. Humphreys, Kenneth D. Karlin, and Steven E. Rokita, J. Am. Chem. Soc. (2002) 124: 6009-6019.

EXAMPLES

Example 1

A compound of Formula I having the following structure, wherein PY is 2-pyridil:

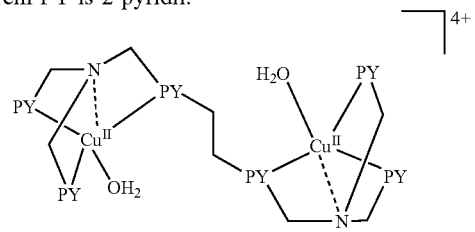

(hereinafter the "binuclear complex") was produced in the following fashion. A methanolic solution (5 mL of Cu(ClO$_4$) 2.6H$_2$O) (0.25 g, 0.67 mmol) was added dropwise to a test tube containing a 5 mL solution of a ligand of formula II having the following structure:

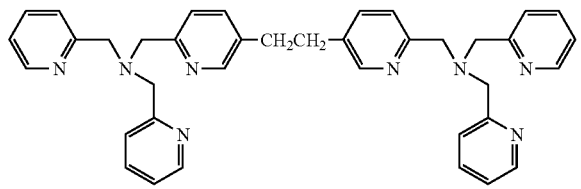

(0.2 g, 0.3 mmol) in MeOH. After one hour at room temperature, blue crystals developed and were isolated by filtration, washed with Et$_2$O and dried in vacuo to yield 0.35 g of a crystalline solid (88%).

Example 2

Copper-dependent strand scission was tested by combining various concentrations of the binuclear copper complex with a labeled DNA sample (preferably 10 nM-10 mM, more preferably 1-10 μM, and preferably 1 μM, and preferably 1-1000, and more preferably 90 nCi) in a sodium phosphate buffer (preferably 10 mM, pH 7.5) and strand scission was initiated by the addition of a reductant (5 mM), which is preferably a thiol, and more preferably mercaptopropionic acid (MPA). Preferably the reductant is 10 nM-100 μM and preferably 100 nm-10 μm, and more preferably 1 μM. The reaction was quenched after a 15 minute incubation at ambient temperature with the addition of 10 mM of diethyl dithiocarbanic acid (5 μL). The DNA was then isolated by ethanol precipitation and then dried under high vacuum. The isolated DNA was then suspended in water, normalized to 45 nCi per sample, mixed with a loading buffer (0.25% bromphenol blue, 0.25% xylene cyanole, 3% sucrose, and 7 M urea). The samples with loading buffer were then separated by denaturing (7 M urea) polyacrylamide (20%) gel electrophoresis and visualized by auto radiography and PhosphorImager (Molecular Dynamics). Quantitation of the products relied upon ImageQuant software.

Specific strand scission was observed on the 3' strand at A$_{24}$ of the frayed duplex Ia (see attached FIG. 1) during reaction with the binuclear complex and 5 mM for 15 minutes at ambient temperature. It was determined that the site that was preferably cleaved is on the 3' overhang and is displaced from the central duplex by one intervening molecule. It was also determined that reaction with the 5' strand of Ia did not result in specific cleavage. However, the binuclear complex did demonstrate weak recognition of the junction between the helix coil by its slightly enhanced level of cleavage at high concentrations of the complex.

Example 3

The binuclear complex was tested against a cell line of 60 human tumor cells. These tests were carried out by the National Institutes of Health (in particular, the National Cancer Institute) in which the compounds were tested against 60 human tumor cell lines at a minimum of five concentrations at 10-fold dilutions. A 48 hour continuous drug exposure protocol was used and a sulforhodamine B (SRB) protein assay was used to estimate cell viability or growth. After conducting these tests, it was determined by the National Cancer Institute that the binuclear complex had effect against cancerous cells.

Example 4

The binuclear complex was tested using in vivo hollow fiber assays performed by the Developmental Therapeutics Program. These tests were carried out by the National Institutes of Health (in particular, the National Cancer Institute) and the IP score was 24. The Total Score was 24. After conducting these tests, it was determined by the National Cancer Institute that the binuclear complex had effect against cancerous cells.

We claim:
1. A method of treating a cancer selected from the group consisting of leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer, in a patient in need thereof, said method comprising administering to a patient a cancer-treating effective amount of a compound of formula (I), wherein the compound of formula (I) is:

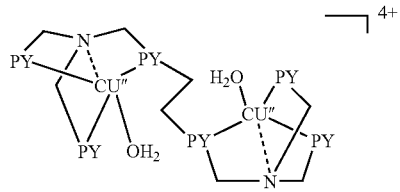

and wherein PY is 2-pyridyl.

2. A method of treating a cancer tumor, wherein the cancer tumor is selected from the group consisting of leukemia tumor, non-small cell lung tumor, colon cancer tumor, central nervous system cancer tumor, melanoma tumor, ovarian cancer tumor, renal cancer tumor, ovarian cancer tumor, cancer tumors of the head and neck, bladder cancer tumor, small cell cancer tumor of the lung, squamous-cell carcinoma tumors of the head, neck, esophagus, skin, and the genitourinary tract, including the cervix, vulva, scrotum, and penis, prostate cancer tumor, and breast cancer tumor, said method comprising administering to the cancer tumor a cancer tumor-treating effective amount of a compound of formula (I), wherein the compound of formula (I) is:

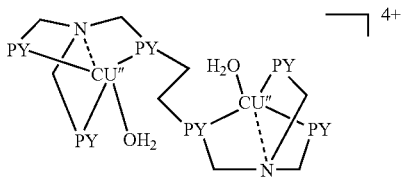

and wherein PY is 2-pyridyl.

3. A method of treating cancer cells, wherein the cancer cells selected from the group consisting of leukemia cells, non-small cell lung cancer cells, colon cancer cells, central nervous system cancer cells, melanoma cells, ovarian cancer cells, renal cancer cells, ovarian cancer cells, cancer cells of the head and neck, bladder cancer cells, small cell cancer cells of the lung, squamous-cell carcinoma cells of the head, neck, esophagus, skin, and the genitourinary tract, including the cervix, vulva, scrotum, and penis, prostate cancer cells, and breast cancer cells, said method comprising administering to the cancer cells a cancer cell-treating effective amount of a compound of formula (I), wherein the compound of formula (I) is:

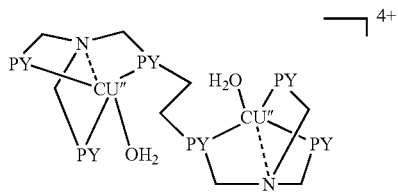

and wherein PY is 2-pyridyl.

4. A method of splitting a nucleic acid segment at a specific position thereon, wherein said method comprises
  (a) providing a nucleic acid segment having (i) an n position, wherein said n position is (a) the first unpaired position on the 3' overhang of the nucleic acid segment, (b) adjacent to the point of scission, and (c) occupied by a guanine residue, and (ii) an x position, wherein said x position is (a) the first unpaired position on the 5' overhang of the nucleic acid segment, (b) adjacent to the point of scission, and (c) occupied by an adenine residue; and (iii) an n+1 position wherein said n+1 position is the point of scission and is the first unpaired residue that is adjacent to the n position;
  (b) contacting the nucleic acid segment with a compound of formula (I) for a time sufficient to split the nucleic acid at the n+1 position of the nucleic acid segment, wherein the compound of formula (I) is:

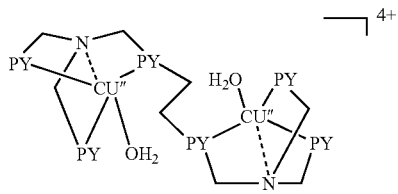

and wherein PY is 2-pyridyl.

5. A method of treating a cancer selected from the group consisting of leukemia, non-small cell lung cancer, colon cancer, central nervous system cancer, melanoma, ovarian cancer, renal cancer, ovarian cancer, cancer of the head and neck, bladder cancer, small cell cancer of the lung, squamous-cell carcinomas of the head, neck, esophagus, skin, and the genitourinary tract, including the cervix, vulva, scrotum, and penis, prostate cancer, and breast cancer, in a patient in need thereof, said method comprising administering to a patient a cancer-treating effective amount of a compound of formula (II), wherein the compound of formula (II) is:

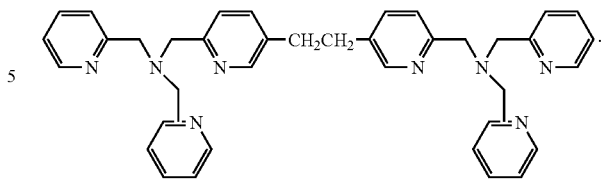

6. A method of treating a cancer tumor, wherein the cancer tumor is selected from the group consisting of leukemia tumor, non-small cell lung cancer tumor, colon cancer tumor, central nervous system cancer tumor, melanoma tumor, ovarian cancer tumor, renal cancer tumor, ovarian cancer tumor, cancer tumors of the head and neck, bladder cancer tumor, small cell cancer tumor of the lung, squamous-cell carcinoma tumors of the head, neck, esophagus, skin, and the genitourinary tract, including the cervix, vulva, scrotum, and penis, prostate cancer tumor, and breast cancer tumor, said method comprising administering to the cancer tumor a cancer tumor-treating effective amount of a compound of formula (II),
wherein the compound of formula (II) is:

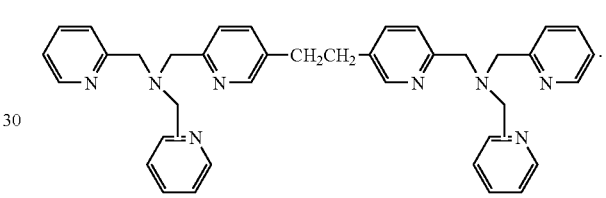

7. A method of treating cancer cells, wherein the cancer cells selected from the group consisting of leukemia cells, non-small cell lung cancer cells, colon cancer cells, central nervous system cancer cells, melanoma cells, ovarian cancer cells, renal cancer cells, ovarian cancer cells, cancer cells of the head and neck, bladder cancer, small cell cancer cells of the lung, squamous-cell carcinoma cells of the head, neck, esophagus, skin, and the genitourinary tract, including the cervix, vulva, scrotum, and penis, prostate cancer cells, and breast cancer cells, said method comprising administering to the cancer cells a cancer cell-treating effective amount of a compound of formula (II), wherein the compound of formula (II) is:

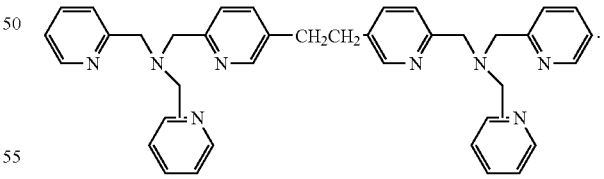

* * * * *